United States Patent [19]
Stephens

[11] Patent Number: 4,518,700
[45] Date of Patent: May 21, 1985

[54] METHOD AND APPARATUS FOR REGULATING THE TEMPERATURE OF AN ANALYTICAL INSTRUMENT REACTOR

[75] Inventor: Donald E. Stephens, Palo Alto, Calif.

[73] Assignee: Beckman Instruments, Inc., Fullerton, Calif.

[21] Appl. No.: 327,378

[22] Filed: Dec. 4, 1981

[51] Int. Cl.³ ............................................. G01N 31/08
[52] U.S. Cl. ........................................ 436/52; 436/89; 422/109; 432/83
[58] Field of Search .................... 422/70, 81, 109, 199, 422/307; 436/52, 89, 90; 432/4, 51, 81, 83, 219; 219/281, 336

[56] References Cited
U.S. PATENT DOCUMENTS

| | | | |
|---|---|---|---|
| 3,431,077 | 3/1969 | Danforth | 23/253 |
| 3,592,046 | 7/1971 | Cramers et al. | 73/23.1 |
| 3,806,321 | 4/1974 | Durrum et al. | 23/253 R |
| 4,014,793 | 3/1977 | Tesarik et al. | 422/70 |
| 4,044,593 | 8/1977 | Haruki et al. | 73/23.1 |
| 4,294,799 | 10/1981 | Stephens et al. | 422/109 |
| 4,312,835 | 1/1982 | Zoltan et al. | 422/70 |

OTHER PUBLICATIONS

LKB44—The Benefits.
Durrum Amino Acid Analyzer Model D-500.
Biotronik Amino Acid Analyser LC 7000.
Chromaspek Instrument by Rank-Hilger.
Model 3A29 Amino Acid Analyzer by Carlo Erba.

Primary Examiner—Hiram H. Bernstein
Attorney, Agent, or Firm—W. H. May; P. R. Harder; T. R. Schulte

[57] ABSTRACT

A temperature control apparatus for a high temperature reactor in an analytical instrument of the type in which a development reagent is added to a flowing stream as part of the detection process. The temperature control apparatus utilizes solid state heat transfer means to transfer heat between a thermoconductive block to which is mounted the reactor and an air exchange heat sink which obtains heat from or disposes heat into ambient air as required. The control apparatus regulates the temperature of the reactor at a very rapid rate in the high temperature range of approximately 90° C. to 150° C. without the use of a separately contained heat exchange medium. The ability of the apparatus to cool the reactor rapidly eliminates the requirement to keep reactor contents at elevated pressures to prevent vaporization of the stream being analyzed.

4 Claims, 10 Drawing Figures

METHOD AND APPARATUS FOR REGULATING THE TEMPERATURE OF AN ANALYTICAL INSTRUMENT REACTOR

BACKGROUND OF THE INVENTION

The present invention is directed to automated analyzers and, more specifically, is directed to a temperature regulator assembly for a stream processing reactor in an analyzing instrument. Color development in the detection system of an amino acid analyzer has been selected as a represented application.

In some amino acid analyzers, a very small or micro chromagraphic column is used as a specialized application of a liquid column chromatographic separation technique, utilizing ion exchange resin as the stationary phase and eluting buffers of varying pH and salt concentration as the moving phase. Amino acids contained in a sample are introduced at the top of the column and are separated from each other as they are eluted through the resin bed which comprises the column packing. For amino acid analysis, the method for detecting the amino acids in the effluent stream has been to combine the column effluent with a reagent that is metered into the stream at a flow rate proportional to that of the column eluent. When the reagent combines with the amino acids present in the stream, compounds are formed which, when subjected to further development process can be detected by specific changes in optical properties such as absorption or fluorescence.

One of the classical detection methods in amino acid analyzer systems is that developed by Spackman and Moore, wherein the reagent used is ninhydrin dissolved in a suitable solvent/buffer solution. Under this process, the column effluent/reagent solution is heated in a reactor to a fixed temperature for a specified period of time. The compound developed as a result of this process will have specific colors, the intensities of which are proportional to the amounts of compounds contained in the flowing stream. The optical density of these compounds is measured at specific wavelengths.

Important to the calibration of the analyzer in terms of its specific sensitivity to detect amino acids is that the fluid/reagent mixture be maintained at a constant elevated temperature for a fixed period of time. It is critical to the stability of the instrument calibration that the two parameters of temperature and exposure time remain constant during the color development process. Classically, this had been accomplished by causing the effluent to pass through a TFE capillary coil which is normally suspended in a boiling water bath to act as the reactor in the amino acid analyzer system.

The separation techniques employed in early analyzers required several hours to complete a single analysis. In such systems, it became common practice to retain the flowing stream within the reactor for as long as fifteen minutes to complete color development. Newer techniques have increased the performance of these analyzers to permit the same analyses to be completed in the order of twenty minutes. It then becomes necessary to provide increased color development in a much shorter period of time. Reference is made to FIG. 1 showing empirical results of studies which relate the optical densities of compounds formed by mixtures of amino acids and ninhydrin as function of development time and temperature.

It may be noted that maximum sensitivity and improved resolution can be obtained by operating the color development reactor at temperatures significantly above 100° C. However, operation at these elevated temperatures introduces several critical problems. It is very important that circumstances must be prevented which would cause or induce the boiling of the liquid passing through the reactor. Further, high temperature in conjunction with the fact that the pH of the solutions alternate between base and acids increases the corrosive nature of the liquids. Also, it is important that the reactor not be damaged by the heat and, therefore, the system must provide rapid cooling of the reactor in the event there is some type of catastrophic loss of fluid flow caused by a loss of control in the system.

Prior approaches utilizing some type of heated bath as the temperature control for a coil shaped reactor are shown in U.S. Pat. No. 3,806,321 (Durrum); No. 4,233,030 (Twitchett); No. 3,926,800 (Stephens); and No. 3,918,907 (Stephens). Attention is also directed to co-pending patent application entitled An Analytical Instrument Temperature Regulator Ser. No. 327,372, filed Dec. 4, 1981, in the names of Donald E. Stephens and Robert J. Ehret and assigned to the assignee of the present invention.

However, these prior systems do not provide the ability to heat to the desirable temperatures above 100° C. with the capability of rapid cool down to prevent boiling of the fluid stream and prevent possible damage to the materials from which the reactor is made.

SUMMARY OF THE INVENTION

The present invention is directed to a temperature regulator apparatus for use in the reactor of automated systems wherein electrical heat transfer means are used to rapidly heat the reactor to 135° C. and rapidly cool it to approximately 95° C. repetitively without causing any detrimental effects on the flowing stream or the reactor material. No moving parts are used and no separate flowing cooling medium is used. The ability of the temperature regulator assembly to quickly respond in heating and cooling eliminates the need for keeping the reactor contents at high pressure to avoid damage to the flowing stream. In a preferable arrangement of the present invention, the reactor is mounted on a thermoconductive block to which is attached a thermoelectric module. In addition, a heat sink is attached to the thermoelectric module in order to promote cooling when required by exiting heat into ambient air.

The control apparatus for the temperature regulator of the reactor is such that a control temperature reference is automatically directed to the power control for the thermoelectric module or modules. Also, a temperature signal system is used for the thermoelectric modules so that this signal can be compared with the reference signal for adjustment of the temperature of the thermoelectric modules to the desired control point. This continuous temperature feedback monitoring and adjustment by the control system provides for the desired temperature regulation of the color development reactor.

The present invention has enhanced response, both in heating and cooling compared to prior systems. Further, the system is designed so that it can operate significantly above 100° C. without damage to the apparatus or the stream being analyzed. The temperature control apparatus for the reactor can maintain the temperature as high as 150° C. with the capability of control cooling as well as rapid cool down in case of power loss to the system.

Of prime importance to the present invention is the recognition that an apparatus utilizing thermoelectric modules and a heat sink made of a block of material can be utilized to provide rapid heating of a reactor to elevated temperatures with the capability of the necessary rapid cool down to avoid possible damage. The present invention utilizes no contained separate heat exchange medium which has to be circulating or flowing adjacent the reactor. The heat exchange is based on convection heating and cooling.

The normal application of thermoelectric modules is usually one of refrigeration where a heat load is brought to a temperature below the local ambient temperature. In such an application, the heat sink must dissipate not only the energy removed from the heat load, but also the energy invested in driving the thermoelectric element. In these systems the temperature difference that can be maintained by the thermoelectric module between its hot and cold junctions is dictated by the particular physical characteristics or properties of the thermoelectric junctions as well as the particular internal heat losses of the device that must be transferred out of the device through the thermoelectric action. In a refrigerator the effect of this internally generated heat is accepted as a reduction in efficiency of the operation of the thermoelectric device. The present invention puts the internal heat generation of the thermoelectric device's operation to a specific beneficial application in making a thermoelectric device operate as a combination heat pump and heat source to heat the reactor to the necessary elevated temperatures.

Because of the high operating temperatures involved, the heat sink has been configured to operate at temperatures significantly above ambient. The control apparatus is capable of precise temperature regulation, rapid heating and cooling, and rapid cool down in the case of power loss to the system.

DETAILED DESCRIPTION OF THE INVENTION

For exemplary purposes, the application of the present invention will be discussed with respect to its use in an amino acid analyzer system. In such a system it is necessary to control the temperature of the thermal reactor to provide desirable color development relating to the flowing stream.

Figure 2:
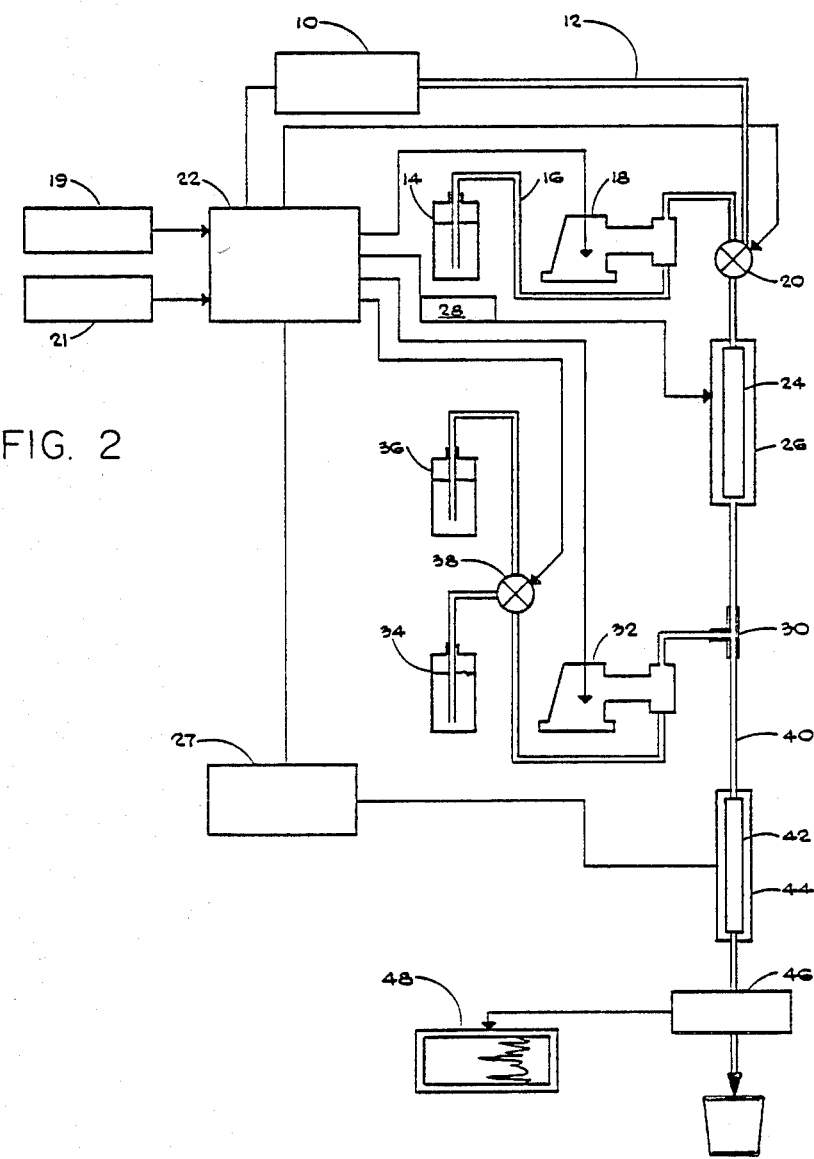
FIG. 2 is a schematic diagram of the overall amino acid analyzer system.

Attention is directed to FIG. 2, showing a schematic view of an overall amino acid analyzer system. A sample table 10 receives various samples for introduction into an automated system which are sequenced through the conduit 12 to the sample injector valve 20. An eluting buffer 14 is transferred through the conduit 16 by the buffer pump 18 into the sample injector valve 20. The sample injector valve 20 is automatically operated by the analyzer controller 22 in order to sequence the sample in conjunction with the eluting buffer for introduction into the chromatographic column 24. As explained previously in the Background of the Invention, the liquid column chromatographic separation technique uses an ion exchange resin as a stationary phase with eluting buffers of varying pH and salt concentration as the moving phase. The column 24 has a temperature regulator apparatus 26. A control system 28 is utilized to regulate the temperature in the column 24.

After the eluting stream exits the bottom of the column 24, it enters into a mixing tee 30 which is in fluid communication with a reagent pump 32 that is designed to pump the reagent 34 into the mixing tee 30. A solvent 36 is also used by operation of the valve 38 to pump solvent into the system which is done during shutdown procedures.

The reagent mixture combined with the eluting buffer 14 from the liquid chromatographic column 24 flows through the conduit 40 into a flow path in the reactor 42. The compounds produced by the reagent mixing with the amino acids are subjected to further development in the reactor where the mixed flowing stream is heated to a specific temperature for a specific time. This enables the detection of the presence of these compounds by noting specific changes in optical properties of the stream. The optical density at specific wavelengths will indicate the amounts of compounds present in the flowing stream. The photometer 46 is used to observe these colors and intensities while the recorder 48 provides a documented record.

Figure 1:
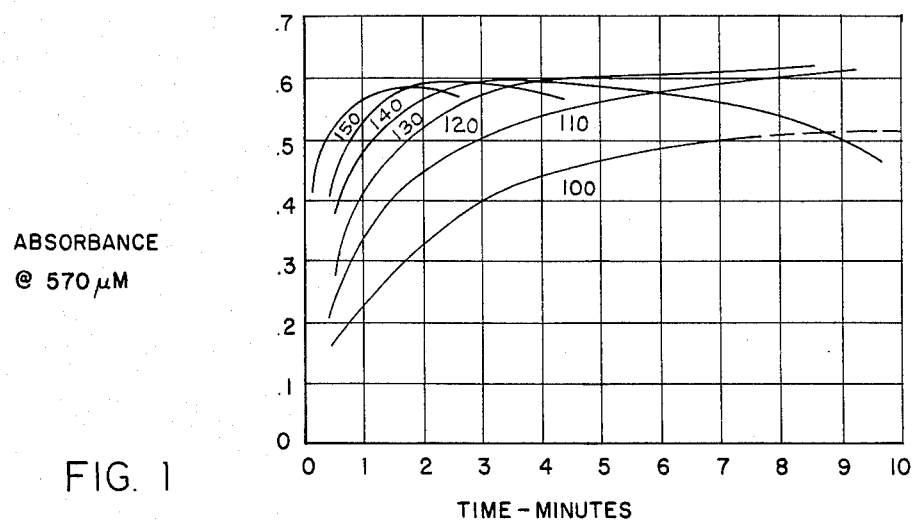
FIG. 1 is a graphic representation of the color development of mixtures of amino acids and ninhydrin for variations in temperature and time.

Reference is made to FIG. 1 showing the results of some empirical studies made of the color development produced in ninhydrin/amino acid compounds under varying conditions of time and temperature. The graphical representation in FIG. 1 is a plot of optical density versus exposure time for a family of curves produced at different temperatures. This chart shows that maximum color development at 100° C. requires a dwell time approaching fifteen minutes within the reactor. However, equivalent development may be realized by heating the mixture to higher temperatures for shorter periods of time, for example, one minute at 135° C.

Figure 5:
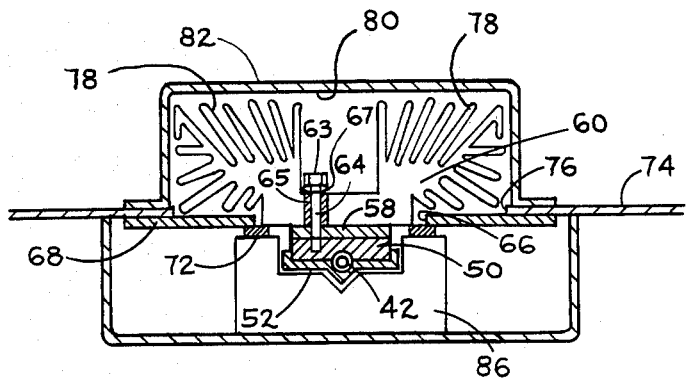
FIG. 5 is a sectional view taken along the line 5—5 in FIG. 3.
Figure 4:
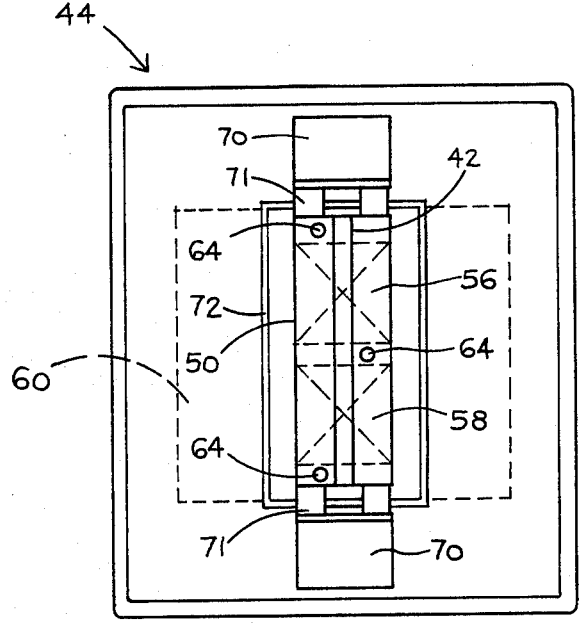
FIG. 4 is a front view of the temperature regulator for the color development reactor.
Figure 3:
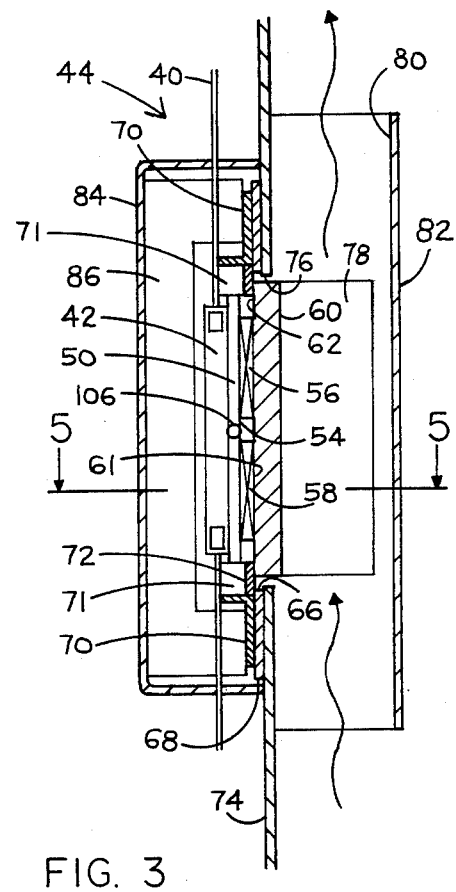
FIG. 3 is a sectional side view of the temperature regulator for the color development reactor.

The requisite temperature control for the reactor 42 is accomplished by the temperature regulator apparatus 44. FIG. 3 shows more detail of the temperature regulator assembly 44. The reactor 42 is clamped to a column or thermal bar 50 by the use of the plate 52 (shown in FIG. 5). The rear face 54 of the column bar 50 is ground flat and polished to provide an excellent thermal junction between the bar and two thermoelectric modules or devices 56 and 58 which are held in compression between the thermal bar 50 and a heat sink element 60. It should be noted that the face 62 of the heat sink is also polished smooth to provide a good thermal junction between the thermoelectric modules 56 and 58 and the heat sink. The thermoelectric modules are clamped between the thermal bar 50 and the heat sink 60 by three stainless steel studs 64 as shown in FIG. 4. The mounting detail of one stud is shown in FIG. 5. The stud 64 is threaded in the bar 50 and insulated from heat sink 60 by insulating sleeve 65. A set of spring washers 67 located between nut 63 and the body of heat sink 60 provide a calibrated compression force when nut 63 is torqued to specifications.

As shown in FIGS. 3, 4 and 5, the reactor 42, thermal bar 50 with the heat sink 60 is inserted through an aperture 66 in the mounting plate 68. Each end of the thermal bar 50 is attached to a mounting bracket 70 by stainless steel screws (not shown) inserted through insulators 71. This arrangement provides thermal isolation between the thermal bar 50 and the mounting plate 68. A flexible seal 72 is then inserted to cover the gap between the heat sink and the mounting plate. This construction provides that the thermal bar 50 is suspended from the mounting plate 68 while the heat sink is, in turn, suspended from the thermal bar. This type of support will remove all lateral stresses from the thermoelectric modules 56 and 58.

Once this overall system has been attached to the support wall 74, the heat sink 60 will protrude through a cutout opening 76 in the support wall. The plurality of heat exchange fins 78 in the heat sink member will be located in a plenum chamber 80 formed by the duct 82. Air leakage from the plenum to the thermal bar is prevented by the seal 72. A cover member 84 having insulation material 86 is attached and surrounds the reactor and reactor bar as shown in FIGS. 3 and 5. A thermistor 106 is located in the central portion of the thermal bar 50 for sensing the temperature of the bar and to serve as a detector for the electrical control system which will control the operation of the thermoelectric modules 56 and 58.

Figure 6:
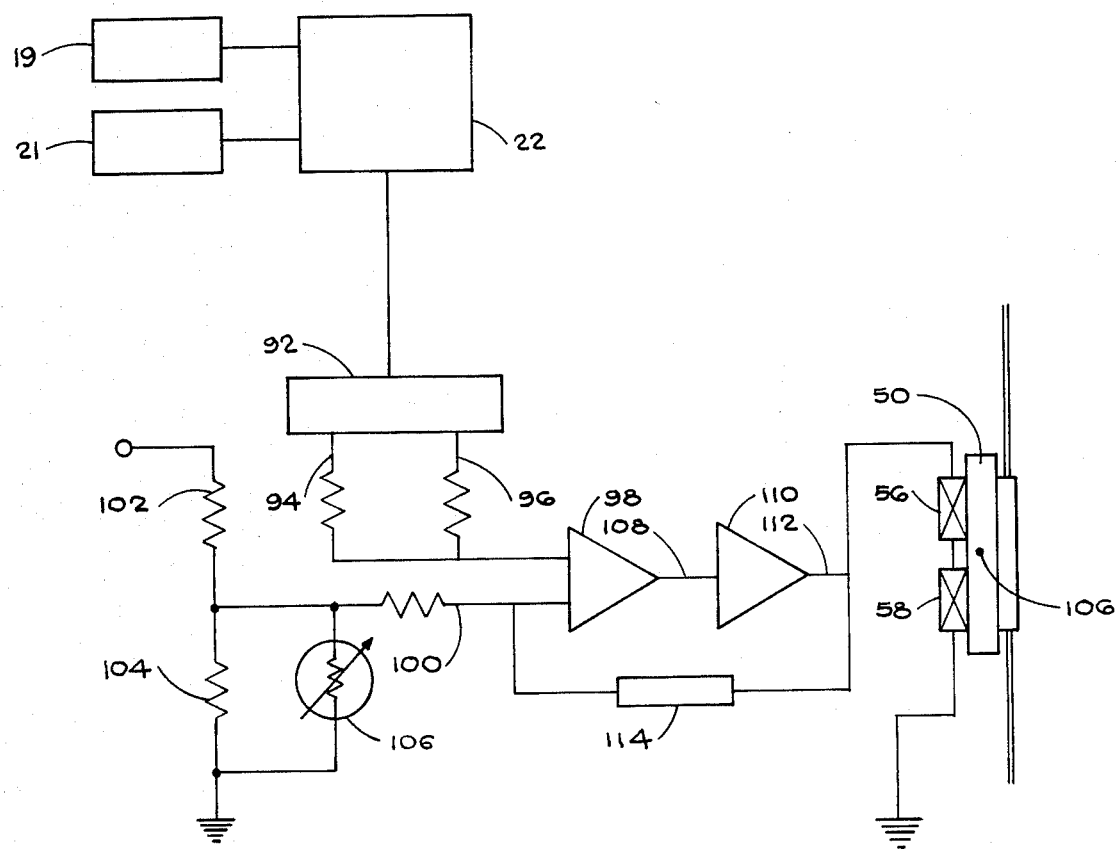
FIG. 6 is a schematic of the control system for the temperature regulator of the present invention.

In FIG. 6 a more detailed schematic is shown with respect to the control system 27 for the regulator assembly 44. The analyzer controller 22 will direct the set point network 92 to select either a low reference input 94 or a high reference input 96 to the operational amplifier 98. The selected reference is compared to the signal 100 that is generated by a feedback bridge comprising the resistors 102 and 104 in conjunction with the thermistor 106. Any difference between the value of selected reference 94 or 96 and the value of the thermistor bridge signal 100 will be amplified by the amplifier 98 in its output 108 to the bidirectional power amplifier 110. The output 112 from the power amplifier 110 will be of a correct value to drive the thermoelectric modules 56 and 58 to maintain the thermistor 106 at the selected reference point. The thermistor 106 is located in a well within the bar 50 located midway between the thermoelectric elements 56 and 58. The low thermal resistance of the thermal bar 50, which is preferably made of copper, in conjunction with the time constants of the feedback network 114, will permit the control system to maintain the reactor temperature with a high degree of precision and stability as required. It should be noted with respect to the bidirectional amplifier 110 in FIG. 6 that the arrangement will allow for the current flowing in the thermoelectric to be reversed if necessary. Therefore, current flowing in one direction in the thermoelectric elements will cause the thermal bar 50 to cool and current flowing in the opposite direction will cause the bar to heat.

The set point network 92 which selects the operating temperature of the reactor has two fixed temperatures 94 and 96 one of which is a low value preferably set at approximately 95° C. and a higher value preferably set at an elevated temperature of approximately 135° C. The operation of the set point network 92 is governed by the analyzer controller 22 which, in addition to selecting the reactor temperature level, also controls the operation of the sample injector 20, the two metering pumps 18 and 32 and the chromatographic column temperature regulator 26 as shown in FIG. 2. Inputs to the analyzer controller 22 are from the operator entered program parameters of 19 or from the analyzer alarm monitor 21.

Normally, when power is input to a thermoelectric device, one inherent characteristic is that there are internal $I^2R$ losses of the device which generate heat that must also be transferred out of the device through conduction and thermoelectric action. In refrigeration this effect ordinarily is considered to be a disadvantage to the thermoelectric device. However, the present invention utilizes this internal heating to advantage in providing the desired operating temperature for the reactor in an amino acid analyzer system.

Experience has shown that operating temperatures of 135° C. afford an optimum compromise of color development and reagent stability. In operation, the temperature differential across the thermoelectric device will be approximately 65°. The heat sink then must be heated to at least 70° which is approximately 45° above normal lab ambient temperature. This represents a significant amount of heat that must be transferred into the heat sink, and it is the $I^2R$ losses within the thermoelectric device which are employed to heat both the heat sink 60 and the reactor 42. In this device, applying power to a correctly designed system will cause the reactor to heat rapidly to the desired temperature with the heat sink flaoting at some temperature below that of the reactor. The temperature of the heat sink will be determined by the temperature differential that can be maintained across the thermoelectric device. Therefore, in the heating mode as power is dissipated in the thermoelectric device, heat is being conducted into both the thermal bar 50 and heat sink 60. In addition, heat is being pumped from the heat sink into the bar by thermoelectric action. Once at operating temperature, the head sink becomes a thermal flywheel which can receive energy from or transfer energy to the thermal bar, as effected by the bidirectional operation of the thermoelectric module.

In those situations where the reactor is required to have rapid cooling from the temperature of 135° C. to a standby temperature of 95° C., the heat sink 60 receives energy from the thermal bar. This energy causes a transient rise in temperature of the heat sink, which can be maintained within acceptable limits by having the correct balance of the thermal mass between the reactor and the heat sink. The temperature of the heat sink would then possibly rise less than 10° C. while the reactor temperature would drop 40° C. The convection losses of the heat sink in addition to the lowered energy input required to maintain the reactor at 95° C. will cause the temperature rise in the heat sink to be dissipated fairly rapidly.

The rapid cooling cycle of the reactor 42 can be initiated through the control system 27 to prevent boiling within the reactor during certain operations of the analyzer. If power is lost, the control inputs are also lost, and momentary boiling conditions may be established within the reactor. By the design of the present invention the arrangement provides for a natural safety device in that the thermoelectric device provides an excellent thermal path for the heat to flow from the reactor to the heat sink when power is off.

When the buffer pump 18 and the reagent pump 32 are operating and the reagent is being metered, the reactor 42 will heat to its high temperature of approximately 135° C. If either of the pumps is turned off or if the reagent pump's selector valve 28 is turned to meter the solvent 36, the reactor will immediately cool to its lower temperature of 95° C. The alarm monitor 21 has input signals from pump pressure transducers (not shown) and a system flow rate monitor (not shown). Any alarm input will cause the reactor to cool immediately to its 95° C. This is important in order to prevent boiling of the stream passing through the reactor, since any vapor bubbles developed would destroy the calibration of the instrument and cause large noise transients which would obliterate the meaningful signal from the record.

Operation of the temerature regulator assembly 44 for the reactor 42 has provided the following capabilities:

Heating time, startup: 23° C. to 135° C.—3 minutes
Controlled cooling time: 135° C. to 95° C.—35 sec.
Recovery heating time: 95° C. to 135° C.—55 sec.
Power off cooling time: 135° C. to 95° C.—2 minutes
Power consumption, startup to 135° C.: 65 watts
Power consumption, equilibrium at 125° C.: 25 watts
Minimum continuous reactor cycle period: 4 minutes Important to the design of the thermal regulator for the color development reactor are certain specifications which dictate the particular configuration and arrangement of the temperature regulator. Power consumption should be kept to a minimum. In the present application of the invention, twenty-five watts at equilibrium is the design limit. Also, it is important that the overall size of the regulator be kept at a minimum for space considerations within an analyzer system. The ratio of thermal capacities of the bar and the heat sink is important with respect to the heat transfer capabilities of the temperature regulator system. In addition, the thermal resistance of the heat sink is important to the dynamics of its heat exchange rate. The thermal resistance of the heat sink will determine how fast the heat sink can dissipate energy that is going into it.

In relation to the above set forth operating capabilities of the temperature regulator, it should be noted that for a seventy watt input the two thermoelectric modules can heat the column block which has a thermal capacitance of approximately sixteen and a half calories per degree centigrade from ambient temperature to 135° C. in about three minutes. At the same time, the heat sink which has a thermal capacitance approximately seven times greater than the column bar will also be heated. If the heat sink were made of even a larger mass wherein its capacitance was increased to a ratio of ten to one with respect to the column bar, the overall temperature regulator would heat somewhat slower initially, but would still be suitable for many applications. Since the heat sink is designed in the preferred arrangement to have a thermal resistance of approximately 1.5° C. per watt, it would require slightly more than twenty-five watts to maintain the heat sink at 40° C. above ambient which is necessary in order to maintain the column bar at 135° C., because of the difference across the thermoelectric module is about 65° to 70°. When the system is operating at equilibrium, the major power consumed is caused by dissipation in the heat sink.

During the programmed or forced cooling of the reactor from 135° C. to 95° C., the heat sink temperature will rise slightly over 20° C. from approximately 40° over ambient to slightly over 60° above ambient. It is important to the present invention that the heat sink dissipate this rise in a suitable period of time. Otherwise, possible repetitive cycling in the operation of the reactor between 95° C. and 135° C. would result in the heat sink being successively increased to temperatures approaching the melting point of solders used in the construction of the thermoelectric modules.

In the present invention the preferred embodiment is designed such that the heat transient of slightly over 20° that is going into the heat sink is dissipated in approximately five minutes. If the thermal resistance were reduced so that the transient recovery would be improved, the result would be the greater power dissipation which in turn would increase the equilibrium power requirement.

In summary, it should be noted that one can increase the capacity of the reactor by using more thermoelectric devices or modules. The transient heat rise in the heat sink can be reduced by increasing its mass. However, this will increase the initial heating time and somewhat the overall repetitive cycle time from 95° C. to 135° C. The transient recovery time of the heat sink can be decreased by reducing its thermal resistance by adding more heat exchange fins. However, this reduced thermal resistance will require increased power requirements. Most of the equilibrium power will be dissipated through the heat sink, since the thermal bar is well insulated and heat losses are minimal.

With respect to overall design characteristics, attention can be directed to keying all major design parameters to a common reference such as power input. In the application shown for the present invention it has been found desirable to maintain the ratio of the total thermal capacitance of both the heat sink and the thermal bar to power input at approximately two calories per degree C. per watt. Further, the ratio of thermal capacitance between the heat sink and the thermal bar should be approximately seven to one.

The dynamic response of the reactor described may be retained in designs of larger or smaller reactors by maintaining these ratios in the new designs. For example, a larger reactor capable of dissipating 100 watts maximum could be designed using larger thermoelectric modules. Its dynamic response would remain the same as that of the reactor described here as long as the total thermal capacitance as well as the ratio of the thermal capacitances of the bar and heat sink are maintained.

Figure 8:
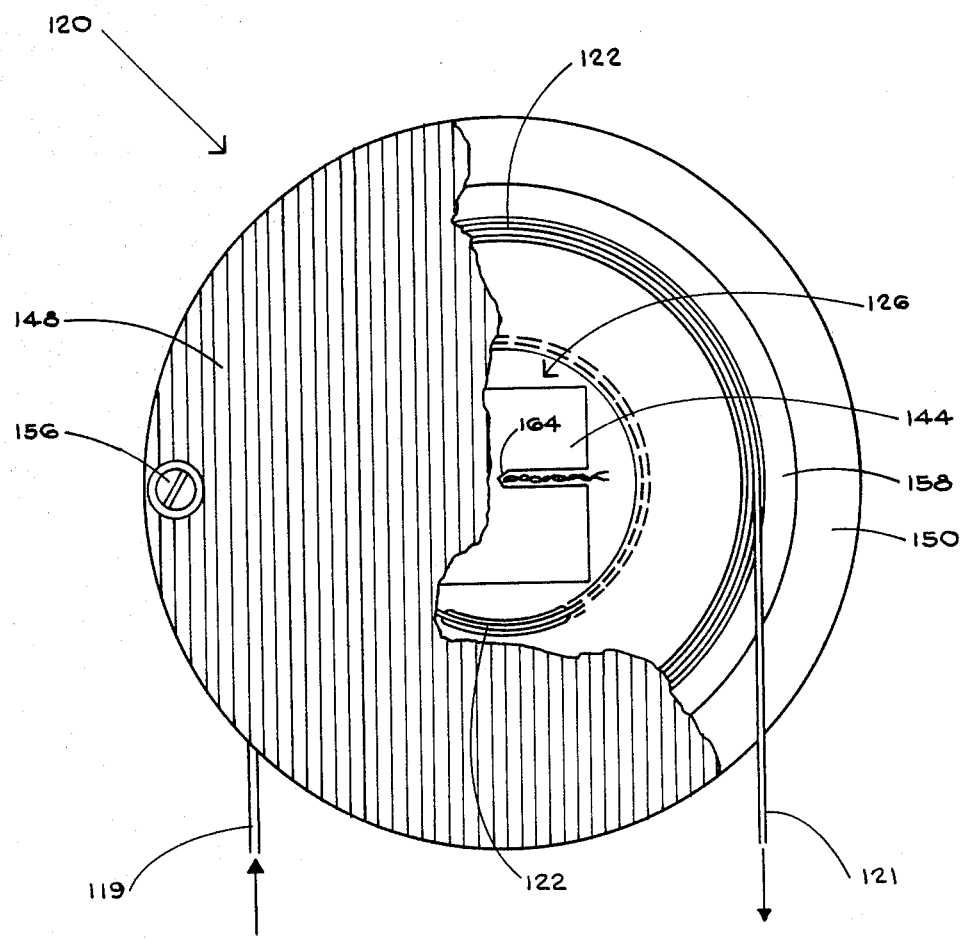
FIG. 8 is a partial cut-away top view of the alternate embodiment shown in FIG. 7.
Figure 7:
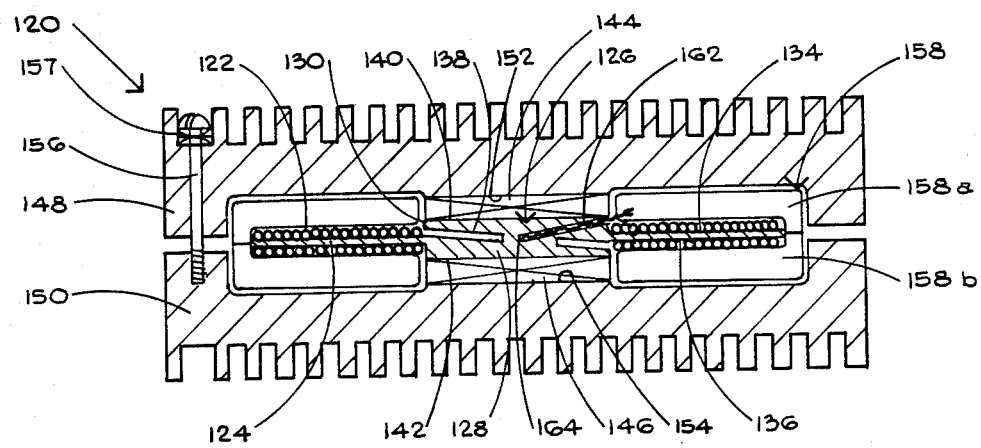
FIG. 7 is a sectional view of an alternate embodiment of the present invention.

FIGS. 7 and 8 show an alternate design for a thermal regulator apparatus of the present invention. In this particular alternate embodiment 120, a capillary tube or coil 122 is used instead of the straight reactor column 42 as shown in the embodiment of FIGS. 3-5. The reactor coil 122 is wrapped in a dual layer flat spiral arrangement and secured in a good thermal bond by a suitable eutectic alloy to the annular flange 124 of a disc member 126 which is preferably made of a copper material. The central portion 128 of the disc member 126 is thicker than the flanged portion 124. The central portion or hub 128 forms an upper shoulder 130 and a lower shoulder 132 with respect to FIG. 7 when interfacing with the thinner annular disc portion 124. The capillary coil is wound in a spiral form beginning adjacent the outer shoulders 130 and 132 of the disc hub 128 and proceeds outward along the respective upper and lower surfaces 134 and 136 of the thin disc portion 124 to form the dual layer of the coil. It should be noted that the coil 122 located above or on the upper surface 134 of the disc portion 124 is in fluid communication with the portion of the coil located on the lower surface 136 of the thin disc portion by a slot 138 extending through the hub portion 128.

The top and bottom surfaces 140 and 142 of the hub portion 128 of the disc 126 are ground flat and polished to provide excellent thermal junction between the disc 126 and two thermoelectric modules 144 and 146 which are located on the opposite sides of the hub portion 128 of the disc. The two thermoelectric modules 144 and 146 are held in compression with the hub portion 128 by two radial heat sinks 148 and 150. Center portions 152 and 154 of the respective heat sinks 148 and 150 are raised and ground flat and polished to provide an excellent thermal junction between the thermoelectric devices and the heat sinks. In addition, a thin film of thermal compound is applied to both faces of the thermoelectric elements 144 and 146 at assembly to further ensure a good thermal contact between the thermoelectric elements with the hub portion 128 of the disc and with the respective heat sinks 148 and 150. The entire system or apparatus is clamped together by a plurality of bolts 156 wherein each bolt has a clearance fit in the heat sink and are threaded into the heat sink. Each bolt assembly is fitted with a set of compression washers 157 which provide a calibrated compressive force to the thermoelectric modules when the system is assembled.

An insulator member 158 encases the coil 122 and occupies the internal cavity 160 which surrounds the thin portion 124 of the disc and the capillary coil 122. The insulator 158 is made of two pieces 158a and 158b. Located in the center of the central hub 128 is a well 162 in which is located a thermistor 164 for sensing the temperature of the disc 126. The disc 126 operates in a similar manner as the thermal bar 50 for the device shown in FIGS. 3-5. As shown in FIG. 8, provision is made in the heat sink portions 148 and 150 as well as in the insulator 158 to accommodate entry 119 and exit 121 in fluid communication with the coil 122.

The overall operation of the device shown in FIGS. 7 and 8 is similar to that set forth in FIGS. 3-5 and the accompanying discussion concerning the temperature regulation of the reactor with respect to the use of thermoelectrics in conjunction with the heat sink.

Figure 10:
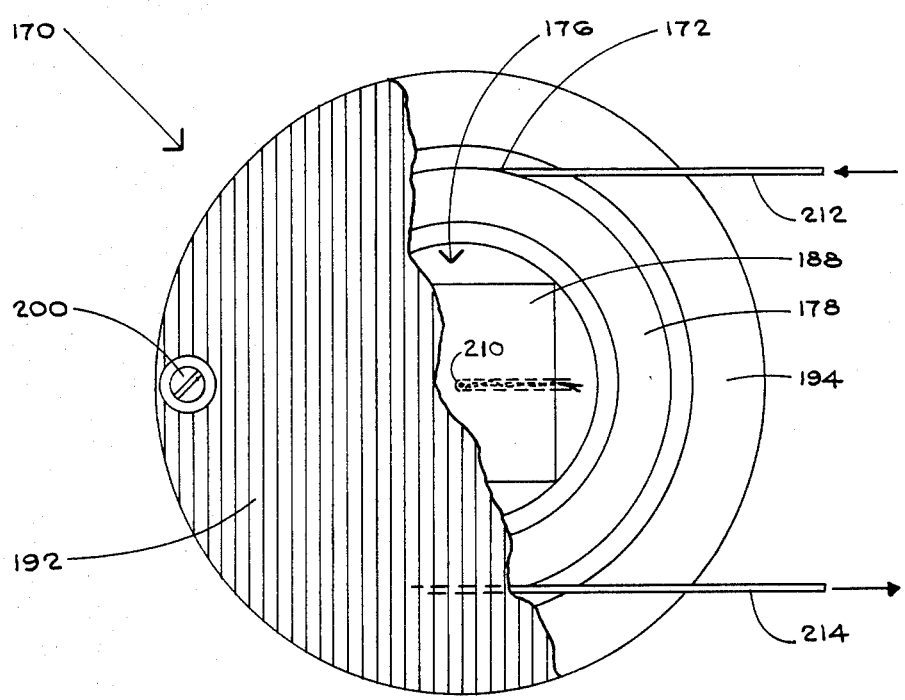
FIG. 10 is a partial cut-away top view of the second alternate embodiment shown in FIG. 9.
Figure 9:
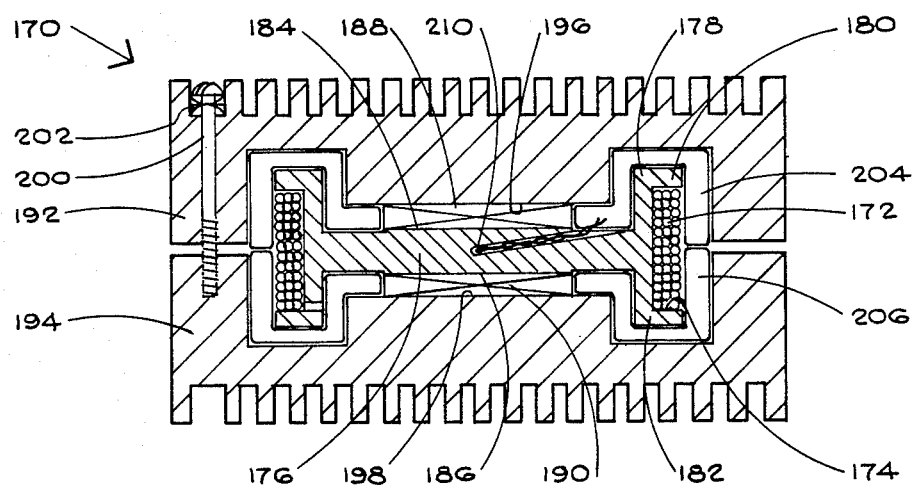
FIG. 9 is a sectional view of a second alternate embodiment of the present invention.

A second alternate embodiment 170 of the present invention is shown in FIGS. 9 and 10 wherein a capillary coil 172 is wound in a layered cylindrical manner within an annular groove or channel 174 in the thermal disc or spool member 176. The capillary coil 172 is secured in a good thermal bond to spool 176 by a suitable eutectic alloy. The spool member 176 is preferably made of copper. The capillary coil 172 is wound three layers deep to provide sufficient length within the heated zone in the reactor arrangement. The spool member 176 has an enlarged annular or rim portion 178 which forms with the two annular flanges 180 and 192 the annular channel 174 for the capillary coil 172. In the center portion of the spool member 176 are raised surfaces 184 and 186 which are ground flat and polished to provide excellent thermal junction between the thermal spool member and respective thermoelectric modules 188 and 190 which are located on opposite sides of the center of the spool member.

The thermoelectric modules are held in compression on the spool member by two radial heat sinks 192 and 194. The interior center portions 196 and 198 of the respective heat sinks 192 and 194 are raised and ground flat and polished to provide excellent thermal junction between the thermoelectric modules and the heat sinks. Further, a thin film of thermal compound is applied to the respective faces of the thermoelectric elements at assembly to ensure good thermal contact between the thermoelectric elements, the thermal spool member and the heat sinks. The overall apparatus is clamped together by three bolts 200 which have a clearance fit in one section of the heat sink, and are threaded into the heat sink. Each of the screw assemblies is fitted with a set of compression washers 202 which provide a calibrated compressive force to the thermoelectric devices when the system is assembled.

Two annular insulating members 204 and 206 are placed between the heat sinks and the thermal spool member. A thermal well 208 is located in the center portion of the spool member 176 to receive a thermistor 210 which is used to sense the temperature of the thermal spool member and serve as the detector for the electronic control system to control the operation of the thermoelectric devices 188 and 190. As shown in FIG. 10, provision is made in the heat sinks 192 and 194 as well as in the insulating members 204 and 206 to accommodate entry 212 and exit 214 in fluid communication with the coil 172.

The operation of the second alternate embodiment 170 of the present invention shown in FIGS. 9 and 10 is similar to that with respect to the alternate embodiment in FIGS. 7 and 8 as well as that shown in the embodiment of FIGS. 3-5.

All of the arrangements set forth in the Figures and discussed above provide a novel arrangement for the operation of a heated reactor in an automated analyzer wherein all electric heating and cooling is utilized with no moving parts and without the need for any separate flowing medium on which the system depends for successful operation.

Consequently, the use of the present type of a heating arrangement for the reactor in an amino acid analyzer system permits the use of elevated temperatures in the color development reactor so that increased analyzer sensitivity and resolution is possible. This can be accomplished without detrimental effects to the flowing stream in the system. Also, the present arrangement allows for the significantly rapid startup which is as high as twenty times faster than presently used systems incorporated in amino acid analyzers. The ability of the system to provide rapid cooling of the reactor eliminates the need to maintain the reactor contents at elevated pressures to prevent vaporization of the stream being analyzed.

Although specific embodiments of the invention have been disclosed, it is envisioned that the basic concept of the present invention of utilizing the thermoelectric arrangement in conjunction with the thermal bar or disc and the heat sink to create the elevated high temperatures for a heated reactor can be incorporated in many embodiments without departing from the scope of the present invention.

What is claimed is:

1. A reactor temperature regulator apparatus for an analytical instrument, said apparatus comprising:

a thermal mounting member;

means attached to said thermal mounting member for providing a flow path for a fluid stream;

solid state heat transfer means attached to said thermal mounting member for heating and cooling said thermal mounting member; and a heat sink block attached to said heat transfer means, the thermal capacitance of said heat sink block being at least seven times the thermal capacitance of said thermal mounting member.

2. A reactor temperature regulator apparatus for an analytical instrument, said apparatus comprising:

a thermal mounting body;

means attached to said thermal mounting body for establishing a flow path for a fluid stream;

solid state heat transfer means attached to said thermal mounting body for heating and cooling said thermal mounting body; and a heat sink block attached to said heat transfer means, the ratio of the total thermal capacitance of said thermal mounting body and said heat sink block to the power input to said heat transfer means being approximately two calories per degree centigrade per watt of power.

3. A color development reactor temperature regulator apparatus for an amino acid analyzer, said apparatus comprising:

a reactor;

means for supporting said reactor;

a thermoelectric module contacting said supporting means;

a heat sink connected to said thermoelectric module, said heat sink, when said thermoelectric module is activated, absorbing a portion of the internal losses generated within said thermoelectric module to cause said heat sink to rise in temperature to provide a high base temperature on one side of said thermoelectric module so that the heating side of said thermoelectric module adjacent said reactor can generate a temperature greater than said high base temperature; and means for controlling said thermoelectric module to provide heating and cooling of said reactor.

4. Method for regulating the temperature of an analytical instrument reactor comprising the steps of:

heating a thermal bar adjacent said reactor;

simultaneously heating a heat sink thermoelectrically coupled to said thermal bar;

pumping heat from said heat sink into said thermal bar until said thermal bar reaches a predetermined temperature; and conducting heat energy from said thermal bar to said heat sink in order to cool said thermal bar to a second predetermined temperature.

* * * * *